US00PP30527P2

(12) United States Plant Patent
Van Dijk

(10) Patent No.: US PP30,527 P2
(45) Date of Patent: May 21, 2019

(54) *ANTHURIUM* PLANT NAMED 'ANTHFOFUN'

(50) Latin Name: ***Anthurium andraeanum* L.**
Varietal Denomination: ANTHFOFUN

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 15/932,788

(22) Filed: Apr. 24, 2018

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./263.1, 365
See application file for complete search history.

(56) References Cited

PUBLICATIONS

UPOV-PLUTO: Plant Variety Database, Jan. 8, 2019, citation for 'Anthfofun'. 1 page.*
EU Community Plant Variety Rights Application No. 2016/2939, Application n°A201603025, filed Nov. 25, 2016, 8 pages.
EU Community Plant Variety Office Official Gazette, I.2017, Feb. 15, 2017, cover page and pp. 30, 50.

* cited by examiner

*Primary Examiner* — Susan McCormick Ewoldt
*Assistant Examiner* — Karen M Redden
(74) *Attorney, Agent, or Firm* — Jondle & Associates, P.C.

(57) ABSTRACT

A new *Anthurium* plant named 'ANTHFOFUN' particularly distinguished by having shiny, unblistered, unique, pink, cordate spathes with green lobes and red tips that retain the original color for a very long period of time, dark green and deltoid durable leaves, dark purple-red spadices with dark red tips, early and rich flowering continuously throughout the year, and a plant height of 35.0 cm to 40.0 cm is disclosed.

3 Drawing Sheets

Genus and species: *Anthurium andraeanum* L.
Variety denomination: 'ANTHFOFUN'.

BACKGROUND OF THE NEW PLANT

The present invention comprises a new and distinct variety of *Anthurium*, botanically known as *Anthurium andraeanum* L., and hereinafter referred to by the variety name 'ANTHFOFUN'. The new *Anthurium* plant is a product of a planned breeding program conducted by the inventor in Bleiswijk, the Netherlands. The objective of this breeding program was to create a new 35.0 cm to 40.0 cm height plant with unique, shiny, pink, cordate spathes with green lobes and red tips.

The new variety originated from a cross-pollination made in August 2009 in Bleiswijk, The Netherlands. The female parent was a pink/red *Anthurium* pot plant designated '15845-02' (unpatented), and the male parent was a green/red *Anthurium* pot plant designated '16653-02' (unpatented).

A single plant was selected from the progeny of the stated cross in July 2011 and has been asexually reproduced repeatedly by tissue culture in Bleiswijk, The Netherlands over a 7-year period. The present invention has been found to retain its distinctive characteristics through successive asexual propagations.

Plant Breeder's Rights for this variety have been applied for in the European Union on Nov. 25, 2016. 'ANTHFOFUN' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Unique, shiny and pink cordate spathes with green lobes and red tips;
2) Dark purple-red spadices with dark red tips;
3) Dark green deltoid leaves; and
4) Spathes that are not blistered.

DESCRIPTION OF THE PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 44-week old plant grown in a greenhouse in Bleiswijk, The Netherlands in March 2018. Colors in the photographs may differ from the color values cited in the detailed botanical description, which accurately describe the actual colors of the new variety.

DESCRIPTION OF THE NEW VARIETY

Figure 1:
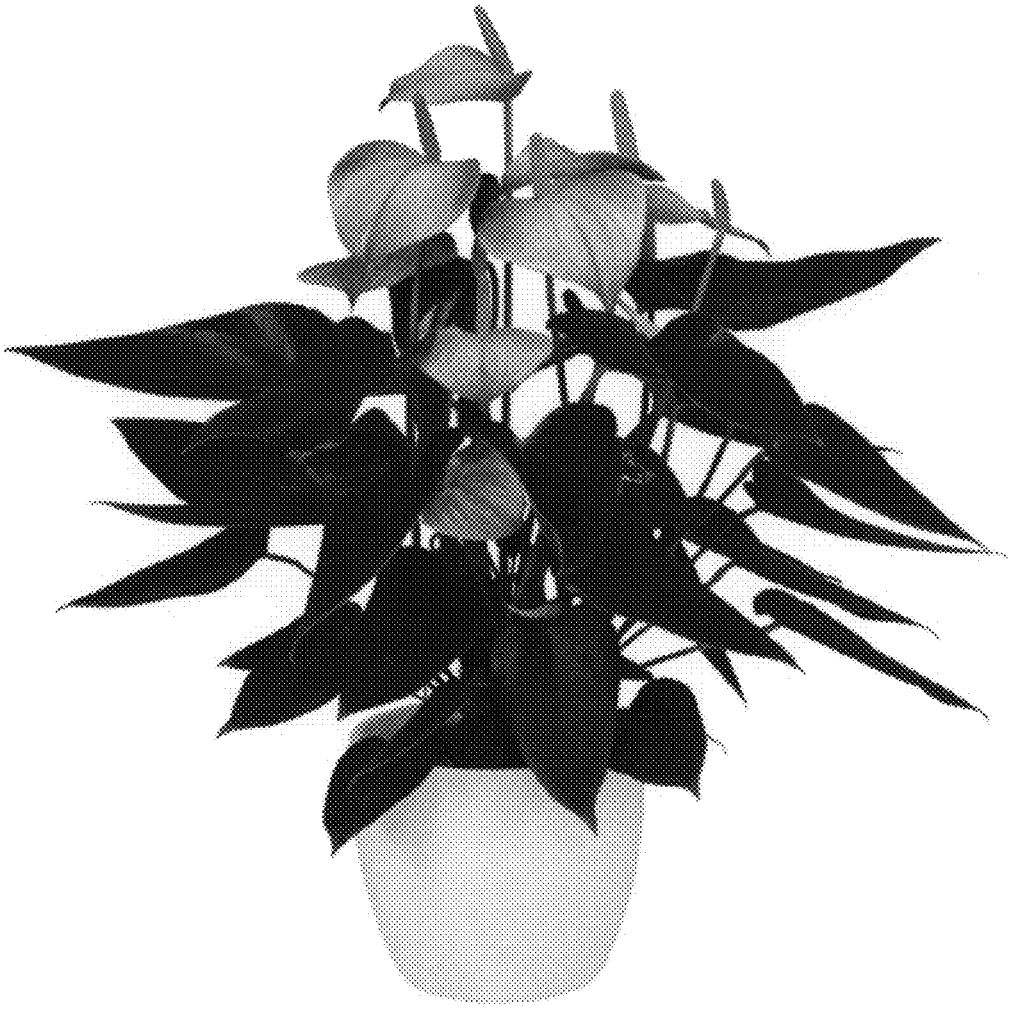
FIG. 1 shows the overall plant habit, including blooms, buds and foliage.
Figure 2:
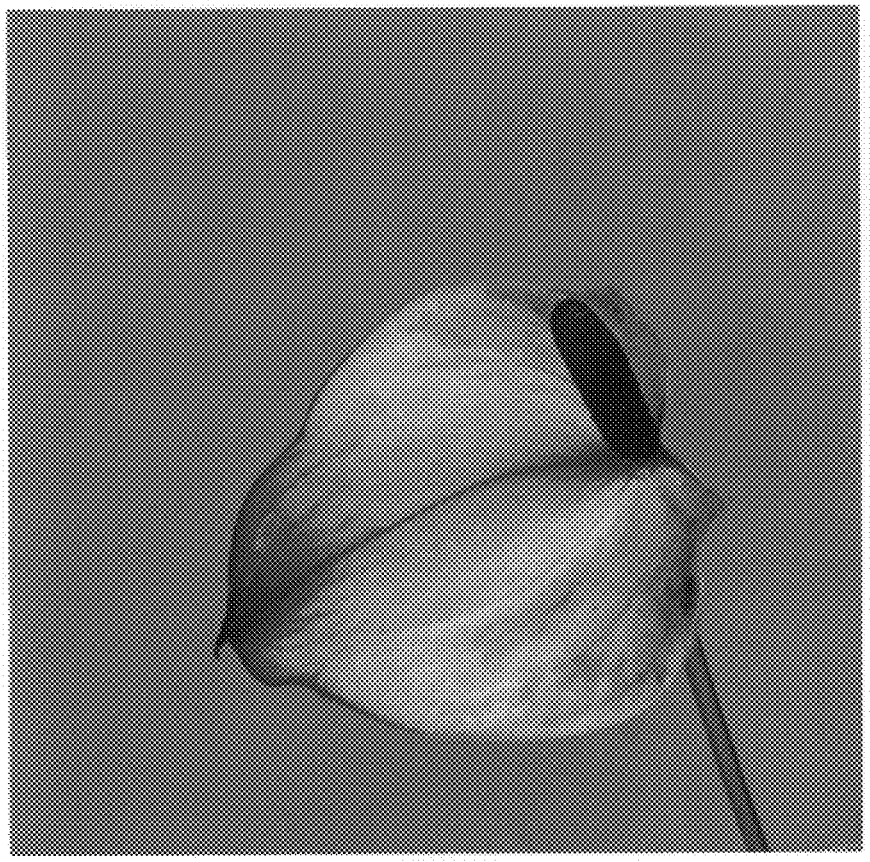
FIG. 2 shows a close-up of the mature spathe.
Figure 3:
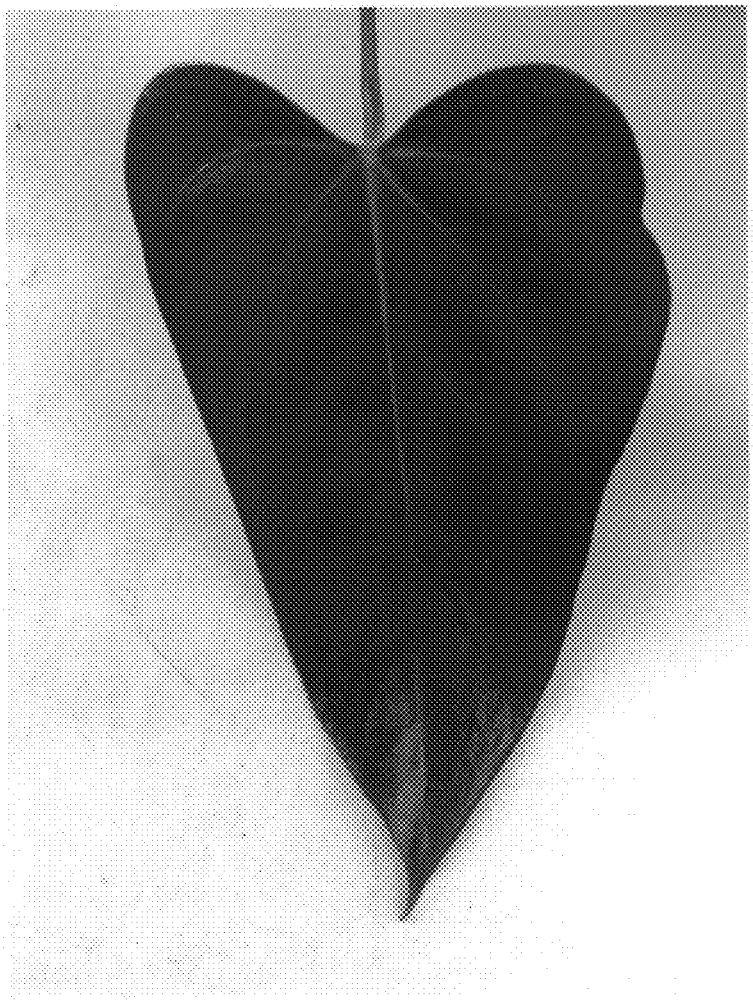
FIG. 3 shows a close-up of the upper leaf blade surface.

The following detailed description sets forth the distinctive characteristics of 'ANTHFOFUN'. The data which define these characteristics were collected from asexual reproductions carried out in Bleiswijk, The Netherlands. The plant history was taken on 44-week old plants which were planted from tissue culture in 14 centimeter (diameter) pots and grown in a glass greenhouse between 19° C. and 24° C. Observations were made in March 2018. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHFOFUN'.

Parentage:

*Female parent*.—*Anthurium* plant '15845-02' (unpatented).

*Male parent*.—*Anthurium* plant '16653-02' (unpatented).

Plant:

*Propagation*.—Tissue culture.

*Root description*.—Fleshy-creamy to light pink colored roots with small hairy lateral roots having yellow colored root tips.

*Time to produce a finished flowering plant*.—42 to 46 weeks after planting in a 14 cm (diameter) pot.

*Growth habit*.—Upright.

*Height* (*measured from soil, including inflorescence*).—35.0 cm to 40.0 cm.

*Width* (*measured from leaf tips*).—34.0 cm to 39.0 cm.

Leaves:

*Immature leaves*.—Length: 13.0 cm to 16.0 cm. Width: 8.0 cm to 9.0 cm. Color: Upper surface: RHS 146A with small red tip (RHS 60A). Lower surface: RHS 146B. Texture (both upper and lower surfaces): Shiny.

*Mature leaves*.—Length (fully expanded): 16.0 cm to 19.0 cm. Width: 9.5 cm to 10.5 cm. Shape: Deltoid. Apex: Acuminate. Base: Cordate. Leaf blade angle with the petiole: Between 120 degrees and 150 degrees. Leaf margin: Entire. Color: Upper surface: RHS 147A. Lower surface: RHS 146B. Texture (both upper and lower surfaces): Shiny, leathery and thick. Venation: Pinnate veining; the mid-vein and primary veins (the veins that radiate out from the junction of petiole and leaf) protrude at the underside of the leaf blade. Venation color: Upper surface: RHS 146B. Lower surface: RHS 146C.

*Lobes*.—Present. Arrangement: Leaf blade has two lobes extending past the petiole. The lobes are non-touching. Length of lobes of mature leaf blades: 1.0 cm to 2.0 cm. Width of lobes of mature leaf blades: 3.0 cm to 4.0 cm. Distance from petiole/leaf junction to highest point on lobes of mature leaf: 1.0 cm to 3.0 cm.

*Petiole*.—Cross-section: Round. Diameter: 0.3 cm to 0.4 cm. Length: 18.0 cm to 21.0 cm for a mature leaf size. Color: Mature leaf: RHS 144A. Immature leaf: RHS 144B. Cataphyll color surrounding the petiole: Outside: RHS 144C with red tip (RHS 60A). Inside: RHS 144D with red tip (RHS 60B).

*Geniculum*.—Length: 1.5 cm to 2.0 cm. Width: 0.3 cm to 0.4 cm. Color: RHS 144B.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a half year to a year.

Spathe:

*Buds*.—The spathe is tightly rolled around the spadix and extrudes from the peduncle sheath. After the spathe is fully open, the peduncle elongates some extra centimeters (approximately 1 to 3 extra centimeters).

*Arrangement*.—Spathe angle with the peduncle is between 110 degrees and 130 degrees; the spathe stands on a wiry peduncle about 8.0 cm to 12.0 cm above the foliage.

*Shape*.—Cordate.

*Apex*.—Mucronate.

*Base*.—Cordate.

*Texture*.—Shiny and not blistered.

*Margin*.—Undulated.

*Size*.—Length: 8.5 cm to 9.0 cm. Width: 9.0 cm to 9.5 cm.

*Lobes*.—Present.

*Arrangement*.—The spathe has two lobes extending past the peduncle. The lobes are non-touching. Length: 0.5 cm to 1.0 cm. Width: 3.0 cm to 4.0 cm.

*Color*.—Just fully open: Upper surface: RHS 158B and RHS 39D with green lobes (RHS 144A/B) and red tip (RHS 46A/B). Lower surface: RHS 36D with green lobes (RHS 144C/D) and red margin (RHS 46A). This pink color remains for a very long period, at least more than 30 weeks after opening.

Peduncle:

*Shape*.—Erect.

*Cross-section*.—Round.

*Length*.—27.0 cm to 32.0 cm.

*Diameter*.—0.4 cm to 0.5 cm.

*Color*.—RHS 144B.

Flowering time:

*General*.—One small, rooted, untreated tissue culture plant of 8.0 cm tall will flower, depending on season, after 42 to 46 weeks and 5 to 6 blossoms appear. More blossoms appear after some additional weeks so that a full flowering and commercial plant will have 6 to 7 pink spathes with green lobes and red tips. Smaller blossoms may occur on immature plants.

Spadix:

*Size*.—Length: 2.5 cm to 3.5 cm (depending on flower size). Width (at apex): 0.5 cm to 0.6 cm. Width (at base): 0.6 cm to 0.7 cm.

*Shape*.—Columnar.

*Angle from spadix tip to peduncle*.—160 degrees to 180 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 59A. Mature: RHS N79B. Ages to: RHS 184A.

Flowers:

*Quantity per spadix*.—170 to 220.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 184C.

Reproductive organs:

*Stamens*.—Not visible.

*Pollen amount*.—Absent.

*Pistil*.—Quantity: Many. Length: Less than 0.01 cm. Color: RHS 184C.

*Style*.—Not observed to date.

*Stigma*.—Shape: Ovoid. Diameter: Less than 0.01 cm. Color: RHS 184C.

*Ovary*.—Rarely visible.

*Ovary color*.—Not measured.

Fruit and seed set: None observed to date.

Disease and pest resistance: Under commercial conditions, no specific resistance to pathogens or pests common to *Anthurium* has been observed to date.

COMPARISON WITH PARENTAL AND COMMERCIAL VARIETIES

The female parent plant of 'ANTHFOFUN', cultivar '15845-02' (unpatented), is no longer in existence, so a meaningful comparison cannot be made.

The male parent plant of 'ANTHFOFUN', cultivar '16653-02' (unpatented), is no longer in existence, so a meaningful comparison cannot be made.

'ANTHFOFUN' differs from similar commercial variety 'ANTHFAXI' (U.S. Plant Pat. No. 30,112) in that 'ANTHFOFUN' has deltoid shaped leaves, a dark red spadix tip, and cordate spathes that are cream and pink with green lobes and red tips, whereas 'ANTHFAXI' has ovate-cordate shaped leaves, a red spadix tip, and orbicular cordate spathes that are white with red tips and have a lighter red region toward the spadix.

I claim:

1. A new and distinct variety of *Anthurium* plant named 'ANTHFOFUN', substantially as illustrated and described herein.

* * * * *